US008920391B2

(12) United States Patent
Thomason et al.

(10) Patent No.: US 8,920,391 B2
(45) Date of Patent: Dec. 30, 2014

(54) CONTAINER FOR SYSTEM FOR SPRAY COATING HUMAN SUBJECT

(75) Inventors: Scott Thomason, Macedonia, OH (US); Nicholas J. Mastandrea, Chardon, OH (US)

(73) Assignee: Sunless, Inc., Macedonia, OH (US)

( * ) Notice: Subject to any disclaimer, the term of this patent is extended or adjusted under 35 U.S.C. 154(b) by 692 days.

(21) Appl. No.: 12/624,083

(22) Filed: Nov. 23, 2009

(65) Prior Publication Data

US 2010/0122745 A1 May 20, 2010

Related U.S. Application Data

(63) Continuation-in-part of application No. 11/151,995, filed on Jun. 14, 2005, and a continuation-in-part of application No. 11/650,323, filed on Jan. 5, 2007, now abandoned.

(60) Provisional application No. 60/581,219, filed on Jun. 18, 2004, provisional application No. 60/756,304, filed on Jan. 5, 2006.

(51) Int. Cl.

| | |
|---|---|
| ***A61M 35/00*** | (2006.01) |
| *B05B 7/16* | (2006.01) |
| *B05B 7/32* | (2006.01) |
| *B05B 7/24* | (2006.01) |
| *B05B 12/00* | (2006.01) |

(52) U.S. Cl.

CPC ................. *B05B 7/16* (2013.01); *B05B 7/2405* (2013.01); *B05B 7/32* (2013.01); *B05B 12/00* (2013.01); *B05B 7/2497* (2013.01); *A45D 2200/057* (2013.01)

USPC ........... 604/289; 604/540; 604/368; 604/389; 604/249; 604/295; 454/49; 454/50; 454/52; 454/53; 454/54

(58) Field of Classification Search

USPC .......................................... 604/289, 295, 296

See application file for complete search history.

(56) References Cited

U.S. PATENT DOCUMENTS

| | | | |
|---|---|---|---|
| 1,708,624 | A | 4/1929 | Kruse |
| 1,955,140 | A | 4/1934 | McKesson |

(Continued)

FOREIGN PATENT DOCUMENTS

| | | |
|---|---|---|
| DE | 20316174 | 4/2004 |
| ES | 2231034 | 1/2005 |

(Continued)

OTHER PUBLICATIONS

Thomason, Scott; Final Office Action in U.S. Appl. No. 12/623,687, Feb. 22, 2011.

(Continued)

*Primary Examiner* — Tatyana Zalukaeva
*Assistant Examiner* — Ilya Treyger
(74) *Attorney, Agent, or Firm* — Venable LLP; Steven J. Schwarz

(57) ABSTRACT

A container for use in a system for spray coating a human subject includes a container body configured to hold a skin coating composition. The container further includes a first end portion having a male coupling valve, where the male coupling valve is configured to couple to a female fitting disposed in a spraying apparatus, where the male coupling valve is further configured to prevent flow of the skin composition from the container while the male coupling valve is not coupled to the female fitting. The container further includes a second end portion opposite the first end portion and having a vent, where the container is configured for inverted connection to the spraying apparatus such that when the male coupling valve is connected to the female fitting the male coupling valve is at a location below the vent, and where opening of the vent allows airflow into the container as the skin coating composition flows out of the container through the male coupling valve.

7 Claims, 11 Drawing Sheets

(56) References Cited

U.S. PATENT DOCUMENTS

| | | | | |
|---|---|---|---|---|
| 1,982,509 | A | 11/1934 | Frank | |
| 4,076,459 | A | 2/1978 | Adams et al. | |
| 4,142,257 | A | 3/1979 | Mace | |
| 4,282,612 | A | 8/1981 | King | |
| 4,798,341 | A | 1/1989 | Gimple | |
| 4,964,399 | A | 10/1990 | Faimali | |
| 4,967,956 | A | 11/1990 | Mansfield | |
| 4,991,776 | A | 2/1991 | Smith | |
| 4,993,594 | A | 2/1991 | Becker et al. | |
| 5,064,119 | A | 11/1991 | Mellette | |
| 5,074,467 | A | 12/1991 | Geberth et al. | |
| 5,496,214 | A | 3/1996 | Marcreigns | |
| 5,842,682 | A * | 12/1998 | Schennum et al. | 251/149.1 |
| 5,853,215 | A | 12/1998 | Lowery | |
| 5,922,333 | A | 7/1999 | Laughlin | |
| 5,927,565 | A * | 7/1999 | Paczonay | 222/484 |
| 6,085,997 | A | 7/2000 | Mills | |
| 6,199,557 | B1 | 3/2001 | Laughlin | |
| 6,251,374 | B1 | 6/2001 | Laughlin | |
| 6,298,862 | B1 | 10/2001 | Laughlin | |
| 6,302,122 | B1 | 10/2001 | Parker | |
| 6,305,384 | B2 | 10/2001 | Laughlin | |
| 6,328,233 | B1 | 12/2001 | Moy et al. | |
| 6,387,081 | B1 | 5/2002 | Cooper | |
| 6,412,707 | B1 | 7/2002 | Wirz | |
| 6,416,747 | B1 | 7/2002 | Laughlin | |
| 6,431,180 | B2 | 8/2002 | Laughlin | |
| 6,439,243 | B2 | 8/2002 | Laughlin | |
| 6,443,164 | B1 | 9/2002 | Parker | |
| 6,446,635 | B2 | 9/2002 | Laughlin | |
| 6,468,508 | B1 | 10/2002 | Laughlin | |
| 6,474,343 | B2 | 11/2002 | Laughlin | |
| 6,533,189 | B2 | 3/2003 | Kott et al. | |
| 6,540,155 | B1 | 4/2003 | Yahav | |
| 6,554,208 | B1 | 4/2003 | Venuto, Sr. | |
| 6,622,733 | B2 | 9/2003 | Saksa | |
| 6,656,455 | B2 | 12/2003 | Laughlin | |
| 6,752,330 | B2 | 6/2004 | DiMaggio et al. | |
| 6,766,966 | B2 | 7/2004 | You | |
| 6,782,893 | B2 | 8/2004 | Laughlin | |
| 6,799,580 | B2 | 10/2004 | Laughlin | |
| 6,881,417 | B1 | 4/2005 | Laughlin | |
| 6,886,572 | B2 | 5/2005 | Laughlin | |
| 6,899,108 | B2 | 5/2005 | Laughlin | |
| 6,918,897 | B2 | 7/2005 | Severino | |
| 7,004,407 | B2 | 2/2006 | Cooper | |
| 7,041,089 | B2 | 5/2006 | Laughlin | |
| 7,082,948 | B2 | 8/2006 | Laughlin | |
| 7,297,211 | B2 | 11/2007 | Cooper | |
| 7,387,684 | B2 | 6/2008 | Cooper | |
| 7,462,242 | B2 | 12/2008 | Cooper | |
| 7,569,037 | B1 | 8/2009 | Spivak | |
| 7,699,882 | B2 | 4/2010 | Stamper | |
| 7,886,684 | B2 | 2/2011 | Cooper | |
| 7,913,918 | B2 | 3/2011 | Zellner | |
| 7,992,517 | B2 | 8/2011 | Cooper | |
| 8,069,812 | B2 | 12/2011 | Lotterhos | |
| 2002/0000237 | A1 | 1/2002 | Laughlin | |
| 2002/0096186 | A1 | 7/2002 | Von Halem | |
| 2002/0112738 | A1 | 8/2002 | Parker | |
| 2003/0029488 | A1 | 2/2003 | Baird | |
| 2003/0094509 | A1 | 5/2003 | Venuto, Sr. | |
| 2003/0127542 | A1 | 7/2003 | Cooper | |
| 2004/0069321 | A1 | 4/2004 | Maleville | |
| 2004/0073186 | A1 | 4/2004 | Cameron | |
| 2004/0089315 | A1 | 5/2004 | Laughlin | |
| 2004/0116880 | A1 | 6/2004 | Venuto, Sr. | |
| 2004/0232257 | A1 | 11/2004 | Venuto, Sr. | |
| 2004/0241106 | A1 | 12/2004 | Laughlin | |
| 2004/0251272 | A1 * | 12/2004 | Hunter | 222/95 |
| 2005/0022807 | A1 | 2/2005 | Laughlin | |
| 2005/0193945 | A1 | 9/2005 | Coffield | |
| 2005/0252445 | A1 | 11/2005 | Laughlin | |
| 2005/0279865 | A1 | 12/2005 | Thomason | |
| 2006/0005850 | A1 | 1/2006 | Laughlin | |
| 2006/0032439 | A1 | 2/2006 | Burato et al. | |
| 2006/0118039 | A1 | 6/2006 | Cooper | |
| 2006/0124779 | A1 | 6/2006 | Cooper | |
| 2006/0163382 | A1 | 7/2006 | Spivak | |
| 2006/0180682 | A1 | 8/2006 | Burato et al. | |
| 2006/0275555 | A1 | 12/2006 | Colizza | |
| 2007/0107121 | A1 | 5/2007 | Smith | |
| 2007/0125798 | A1 | 6/2007 | McGuire | |
| 2007/0169261 | A1 | 7/2007 | Smith | |
| 2007/0186340 | A1 | 8/2007 | Gay | |
| 2007/0197982 | A1 | 8/2007 | Thomason | |
| 2008/0072376 | A1 | 3/2008 | Guerin et al. | |
| 2009/0031949 | A1 | 2/2009 | Nagase et al. | |
| 2009/0157015 | A1 | 6/2009 | Lotterhos | |
| 2009/0211592 | A1 | 8/2009 | Waters | |
| 2009/0314857 | A1 | 12/2009 | Thomason | |
| 2010/0001097 | A1 | 1/2010 | Spivak | |
| 2010/0122745 | A1 | 5/2010 | Thomason | |
| 2010/0129557 | A1 | 5/2010 | Thomason | |
| 2010/0145529 | A1 | 6/2010 | Thomason | |
| 2010/0266776 | A1 | 10/2010 | Cooper | |
| 2010/0291847 | A1 | 11/2010 | Thomason | |

FOREIGN PATENT DOCUMENTS

| | | |
|---|---|---|
| JP | 2002-205515 | 7/2003 |
| WO | 03013648 | 2/2003 |
| WO | 2004/006932 | 1/2004 |
| WO | 2004/069321 | 8/2004 |
| WO | 2005/094754 | 10/2005 |
| WO | 2006/104705 | 10/2006 |

OTHER PUBLICATIONS

Thomason, Scott; Office Action in U.S. Appl. No. 12/623,687, Sep. 1, 2010.

Thomason, Scott; Final Office Action in U.S. Appl. No. 11/151,995, Nov. 18, 2011.

Thomason, Scott; Office Action in U.S. Appl. No. 11/151,995, Feb. 23, 2011.

The Tanning website (http://www.thetanningstore.com), Airbrush Tanning Kits, Applicant's Counsel became aware of these products in or about Nov. 2004.

Office Action in corresponding U.S. Appl. No. 12/623,687, filed Nov. 23, 2009; dated Feb. 23, 2012.

Office Action in corresponding U.S. Appl. No. 12/624,149, filed Nov. 23, 2009; dated Aug. 7, 2012.

Office Action in corresponding U.S. Appl. No. 12/837,134, filed Jul. 15, 2010; dated Jun. 22, 2012.

Fu, Jennifer M. et al.; "Sunless Tanning"; Journal of the American Academy of Dermatology, vol. 50, Issue 5, May 2004, pp. 706-713.

Webpages associated with www.mist-on.com, published at least as early as Apr. 2004 by Mist-On Systems, Inc., accessed via web archive on Jun. 11, 2013.

Webpages associated with www.mystictan.com, published at least as early as Dec. 2005 by Mystic Tan, Inc., accessed via web archive on Jun. 11, 2013.

Webpages associated with www.magictancorp.com, published at least as early as Jun. 2004, by MagicTan, Inc., accessed via web archive on Jun. 11, 2013.

Webpages associated with www.hollywoodtan.com, published at least as early as Feb. 2005, by Hollywood Tan, Inc., accessed via web archive on Jun. 11, 2013.

Fresh'n Up Model 500003 Parts Guide, published on Aug. 15, 2005 by Industrial Vacuum Systems.

Quick Track Linear Motion System Catalog, published in 2005 by BishopWisecarver.

LoPro Linear Motion System Catalog, published in 2002 by BishopWisecarver.

(56) References Cited

OTHER PUBLICATIONS

*Sunless, Inc.* v. *Heartland Tanning, Inc.*, USDC Eastern District of Texas, Tyler Division, Case No. 6:12-cv-00665-LED; Heartland Tanning, Inc.'s Answer and Amended Counterclaims, Redacted for IDS, filed Jun. 17, 2013.

Marine Plumbing Catalog, published Jan. 2005 by John Guest USA, Inc.

Statement of Related Litigation, U.S. Appl. No. 12/624,083, filed Oct. 4, 2013.

Webpages associated with www.mystictan.com, "The Most Beautiful Tan Under the Sun . . . " published at least as early as Dec. 2005 by Mystic Tan, Inc., accessed via web archive on Jun. 11, 2013.

Webpages associated with www.magictancorp.com, "Serious Tan, Seriously Fast, UV-Free", published at least as early as Jun. 2004, by MagicTan, Inc., accessed via web archive on Jun. 11, 2013.

*Sunless, Inc.* v. *Heartland Tanning, Inc.*, USDC Eastern District of Texas, Tyler Division, Case No. 6:12-cv-00665-LED; Heartland's Initial Invalidity Contentions, filed Jun. 17, 2013.

*Sunless, Inc.* v. *Heartland Tanning, Inc.*, USDC Eastern District of Texas, Tyler Division, Case No. 6:12-cv-00665-LED; Heartland's Appendices A-1 to A-12.

Office Action issued in U.S. Appl. No. 11/151,995 dated Jul. 7, 2014.

* cited by examiner

CONTAINER FOR SYSTEM FOR SPRAY COATING HUMAN SUBJECT

CROSS-REFERENCE TO RELATED APPLICATIONS

This application is a continuation-in-part of U.S. patent application Ser. No. 11/151,995 filed on Jun. 14, 2005, which claims the benefit of priority of U.S. Provisional Application No. 60/581,219 filed on Jun. 19, 2004. This application is also a continuation-in-part of U.S. patent application Ser. No. 11/650,323 filed on Jan. 5, 2007, which claims priority from U.S. Provisional Application No. 60/756,304 filed on Jan. 5, 2006. These applications are hereby incorporated by reference in their entirety herein.

BACKGROUND

Numerous forms of artificial tanning products are currently available, including lotions, creams, gels, oils, and sprays. These products are typically mixtures of a chemically-active skin colorant or a bronzer, in combination with moisturizers, preservatives, anti-microbials, thickeners, solvents, emulsifiers, fragrances, surfactants, stabilizers, sunscreens, pH adjusters, anti-caking agents, and additional ingredients to alter the color reaction.

Automated systems for applying artificial tanning products often include a booth provided with a spraying system. The user selects a tanning shade and intensity before the process begins, then steps inside the booth. Once the user is inside, the spraying system is activated and the user is uniformly coated.

BRIEF DESCRIPTION OF THE DRAWINGS

In the accompanying drawings and descriptions that follow, like parts are indicated throughout the drawings and description with the same reference numerals, respectively. One of ordinary skill in the art will appreciate that one element can be designed as multiple elements or that multiple elements can be designed as one element. An element shown as an internal component of another element can be implemented as an external component and vice versa. The figures are not drawn to scale and the proportions of certain parts have been exaggerated for convenience of illustration.

DETAILED DESCRIPTION

Figure 1:
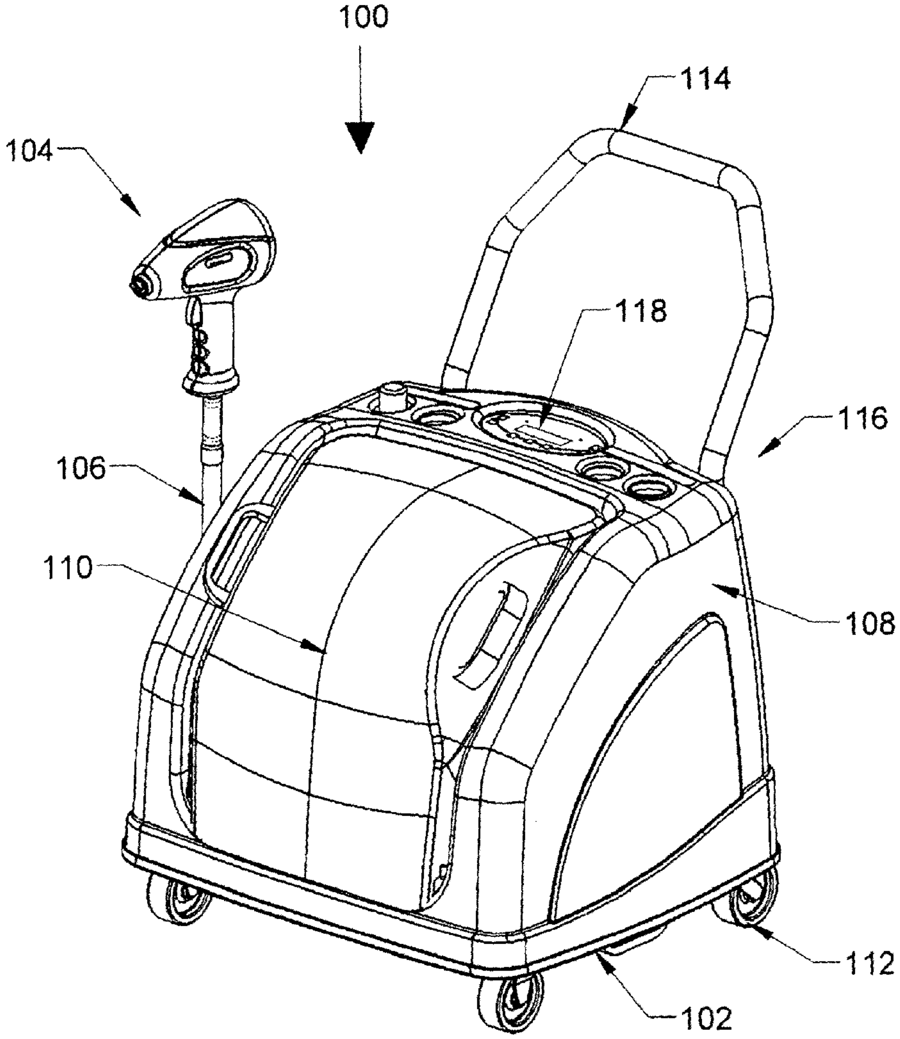
FIG. 1 is a simplified perspective view of one embodiment of a fluid spraying system 100.
Figure 2:
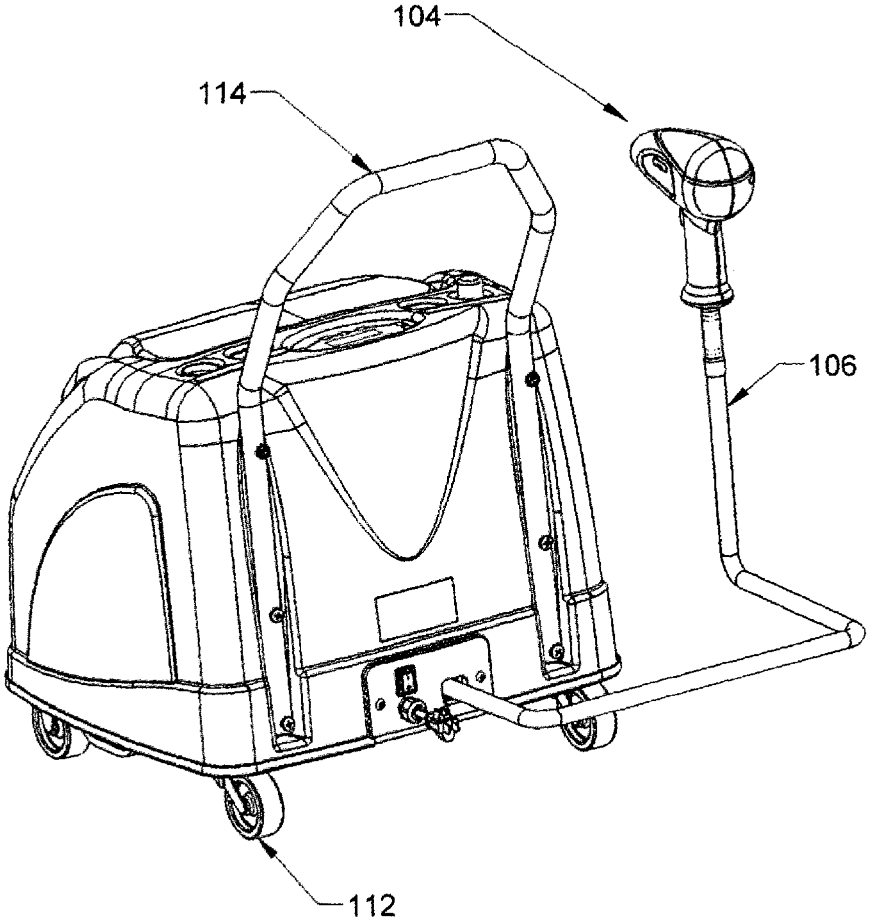
FIG. 2 is a simplified reverse perspective view of the fluid spraying system 100.

FIGS. 1 and 2 illustrate front and rear perspective views, respectively, of one embodiment of a fluid spraying system 100. The system 100 includes a base unit 102 configured to house fluid containers or reservoirs (not shown) and a handheld sprayer assembly 104 in fluid communication with the fluid reservoirs or containers via a hose 106. The system 100 is configured to spray a fluid onto an application surface.

In a preferred embodiment, the fluid spraying system 100 can be employed as a sunless tanning spraying system where it is configured to spray a sunless-tanning solution onto a human body. Exemplary sunless-tanning solutions include one or more colorants, such as dihydroxyacetone, crotonaldehyde, pyruvaldehyde, glycolaldehyde, glutaraldehyde, otho-phthaldehyde, sorbose, fructose, erythrulose, methylvinylketone, food coloring, or any other available colorant. The sunless-tanning solutions can additionally or alternatively include one or more bronzers, such as lawsone, juglone, or any other available bronzer. It will be appreciated that the sunless-tanning solutions can include additional ingredients, such as moisturizers and scents, to make the solution more appealing to a user.

While the preferred embodiment can be employed as a sunless tanning spray system, the system 100 can also be employed to spray other fluids onto the human body. For example, the system 100 can be configured to spray sunscreens, suntan lotions, tanning accelerators, sunburn treatments, insect repellants, skin toners, skin bleaches, skin lighteners, anti-microbial compositions, moisturizers, exfoliants, nutriments or vitamins, massage aides, muscle relaxants, skin treatment agents, burn treatment agents, decontamination agents, cosmetics, or wrinkle treatments or removers.

In one embodiment as shown in FIGS. 1 and 2, the base unit 102 can be in the form of a mobile cart that includes a support platform (not shown), a housing 108, and a door 110 configured to allow a user to access the fluid containers (not shown) housed in the base unit 102. Optionally, the mobile cart can include a plurality of wheels 112, a push handle 114, and a holder tray 116. The holder tray 116 can be contoured, as shown in FIG. 2, to hold the sprayer assembly 104 in either a sideways or downward orientation. An input/output device 118 such as an LCD touchpad display can be located on the top portion of the mobile cart to provide information to and accept commands from the user.

Figure 3:
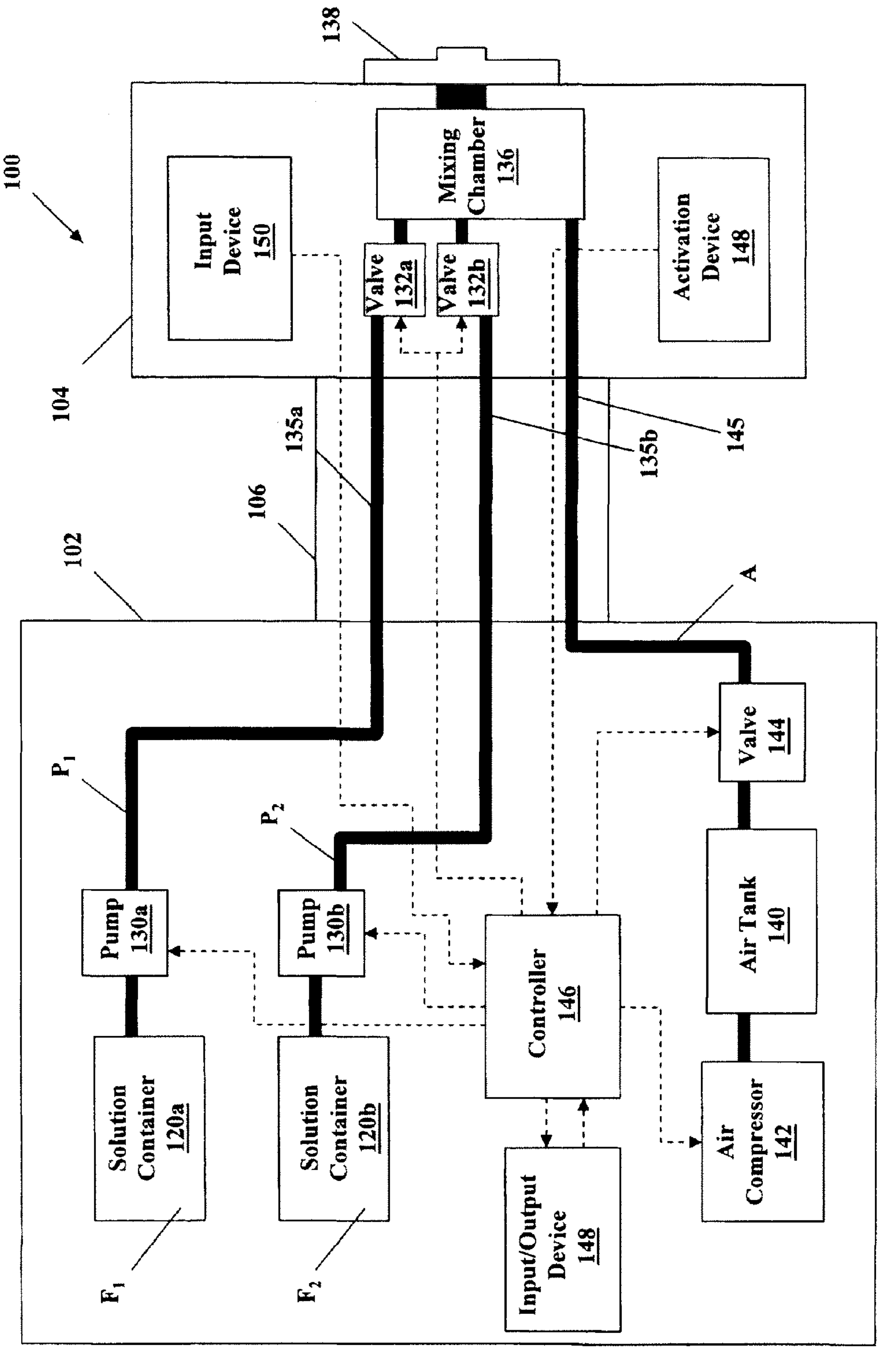
FIG. 3 is a simplified schematic view of one embodiment of the internal components of the fluid spraying system 100.

FIG. 3 is a simplified schematic depicting the internal components of one embodiment of the fluid spraying system 100. In this embodiment, the system 100 includes first and second fluid containers 120*a,b* provided in the base unit 102. The first and second fluid containers 120*a,b* are each configured to hold a fluid. For example, the first and second fluid containers 120*a,b* hold a first fluid $F_1$ and a second fluid $F_2$, respectively. It will be appreciated that the base unit 102 can house a single fluid container or more than two fluid containers.

In one embodiment, the fluid containers 120*a,b* can hold sunless-tanning solutions as described above. For example, each fluid container 120*a,b* can hold a different sunless-tanning solution. The different tanning solutions can have different chemical compositions which effect the hue of the resulting tan. Alternatively, one fluid container (e.g., the first fluid container 120*a*) can contain water or another dilution agent to dilute the tanning solution contained in the second solution container (e.g., the second fluid container 120*b*). The contents of the different fluid containers can be mixed in various combinations to provide a range of shades, thereby allowing the user to select a preferred tanning shade. It will be appreciated that the fluid containers 120*a,b* can the same sunless-tanning solution.

Figure 4:
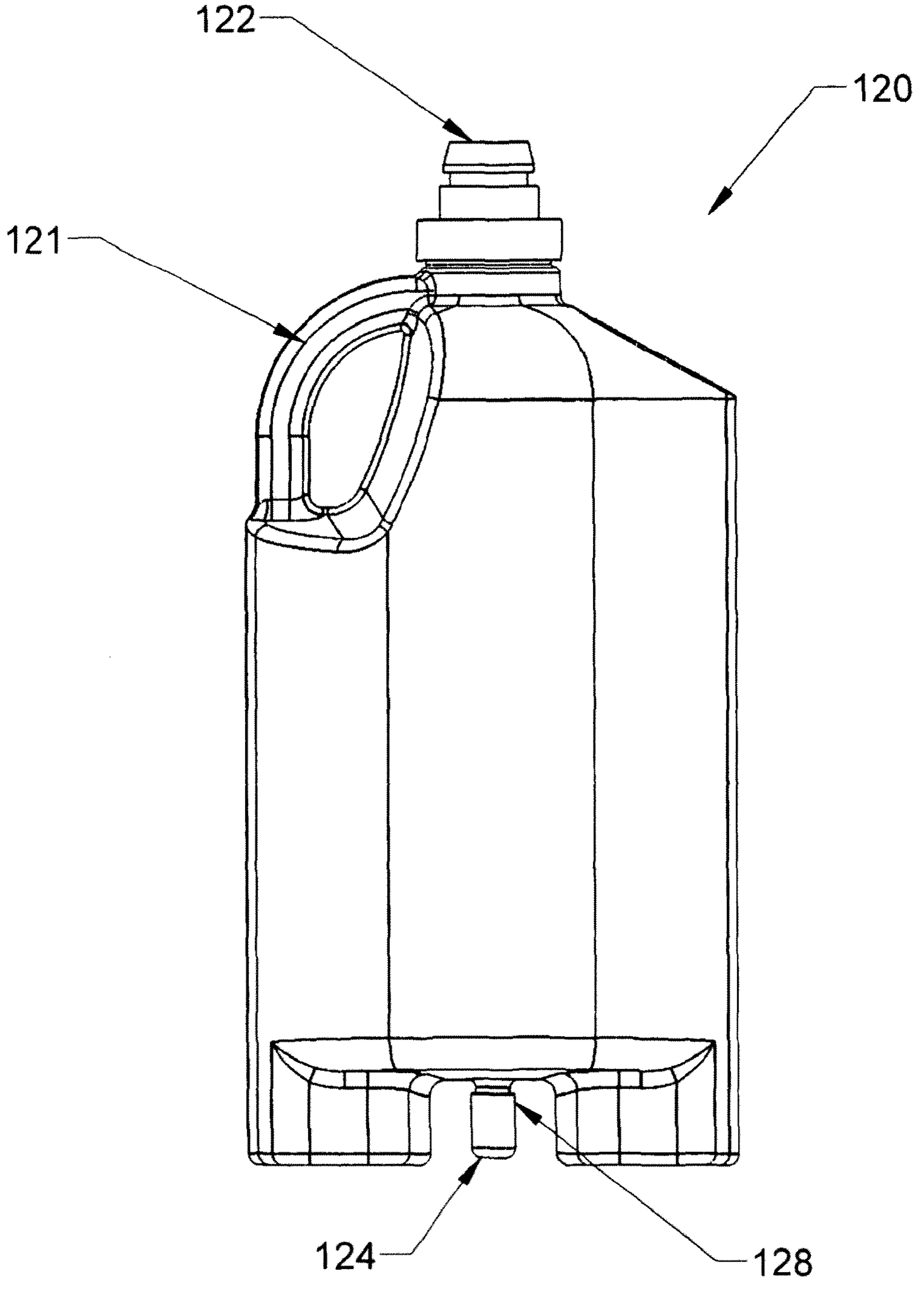
FIG. 4 is a side view of one embodiment of a fluid container 120.

FIG. 4 illustrates a side view of one embodiment of a fluid container 120. In this embodiment, the fluid container 120 includes a handle 121, a male quick disconnect valve 122 at an opening located at one end portion of the fluid container 120, and a vent 124 provided at the other end portion of the fluid container 120. The fluid container 120 can also include a check valve 128 to ensure that fluid flows in only one direction such that, when the fluid container 120 is empty, the check valve 128 will prevent any residual solution from leaking out when the fluid container 120 is removed. It will be appreciated that the fluid container 120 can be configured differently in shape and size from the one illustrated in FIG. 4. Also, it will be appreciated that different fittings such as interchange couplings, poppet couplings, or threaded couplings, can be used to dispense solution from the fluid container 120.

In one embodiment, the fluid containers 120*a,b* are removable. Alternatively, the base unit 102 can house fixed fluid containers that can be filled with a fluid while still in the base unit 102 when the fluid level falls below a predetermined threshold.

Figure 5:
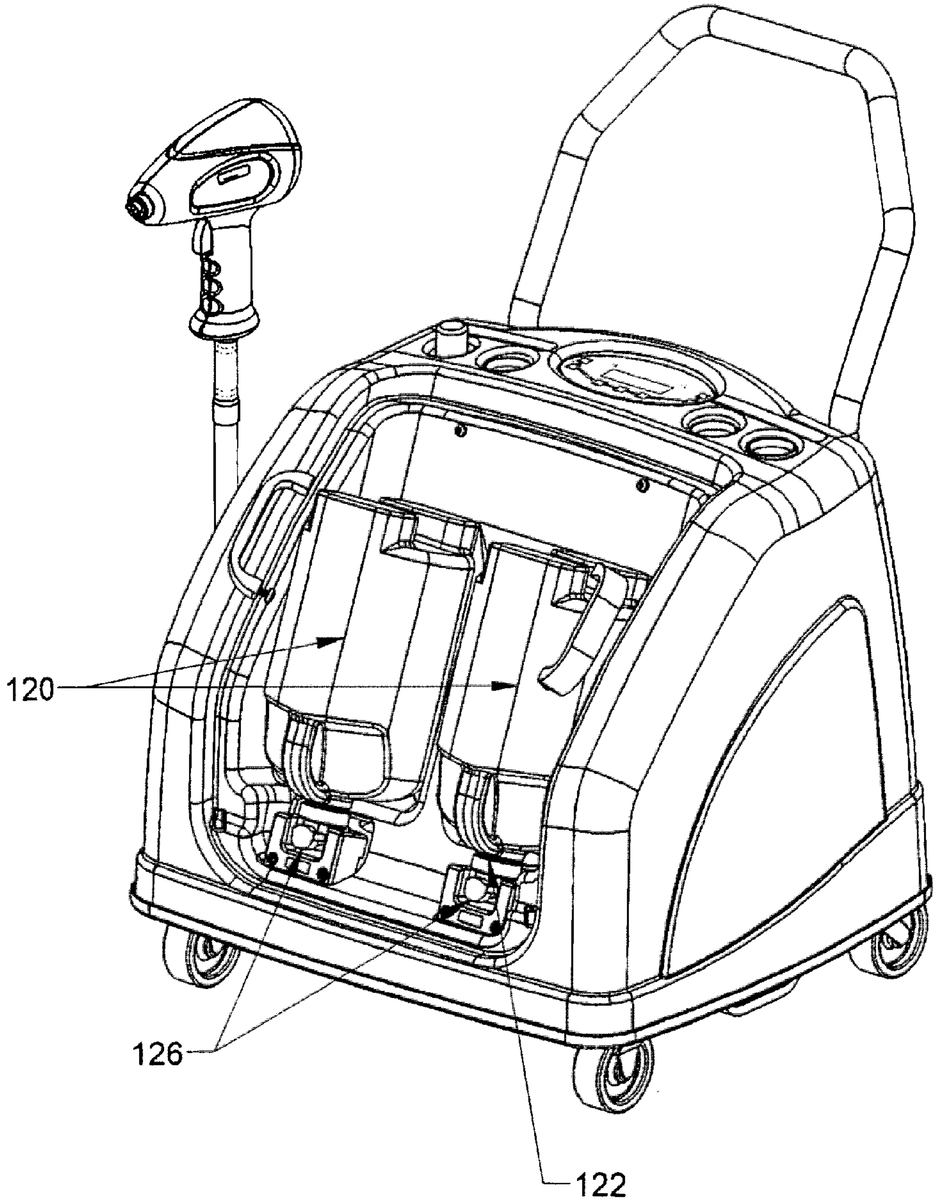
FIG. 5 is a simplified perspective view of one embodiment of the fluid spraying system 100 with a door removed from the base unit 102 to expose the fluid containers.

FIG. 5 illustrates a simplified perspective view of the fluid spraying system 100 with the door 110 removed to expose the fluid containers 120*a,b*. As shown in FIG. 5, each fluid container 120*a,b* is inverted such that the male quick disconnect valve 122 mates with a female quick disconnect fitting 126 disposed in the base unit 102. When a new fluid container 120 is added to the system 100, the male quick disconnect valve 122 of the fluid container 120 is snapped into the female quick disconnect fitting 126 in the base unit 102. The vent 124 on the fluid container 120 can then be opened to equalize the air pressure inside the fluid container 120, allowing fluid to flow freely.

With reference back to FIG. 3, the system 100 can include first and second pumps 130*a,b* provided in the base unit 102. The first pump 130*a* is configured to pump the first fluid $F_1$ held in the first fluid container 120*a* along a fluid flow path $P_1$ through the hose 106 to the sprayer assembly 104, while the second pump 130*b* is configured to pump the second fluid $F_2$ held in the second fluid container 120*b* along a fluid flow path $P_2$ through the hose 106 to the sprayer assembly 104. In one embodiment, the pumps 130*a,b* are positive displacement pumps. It will be appreciated, however, that any other type of fluid pump may suffice.

Figure 6:
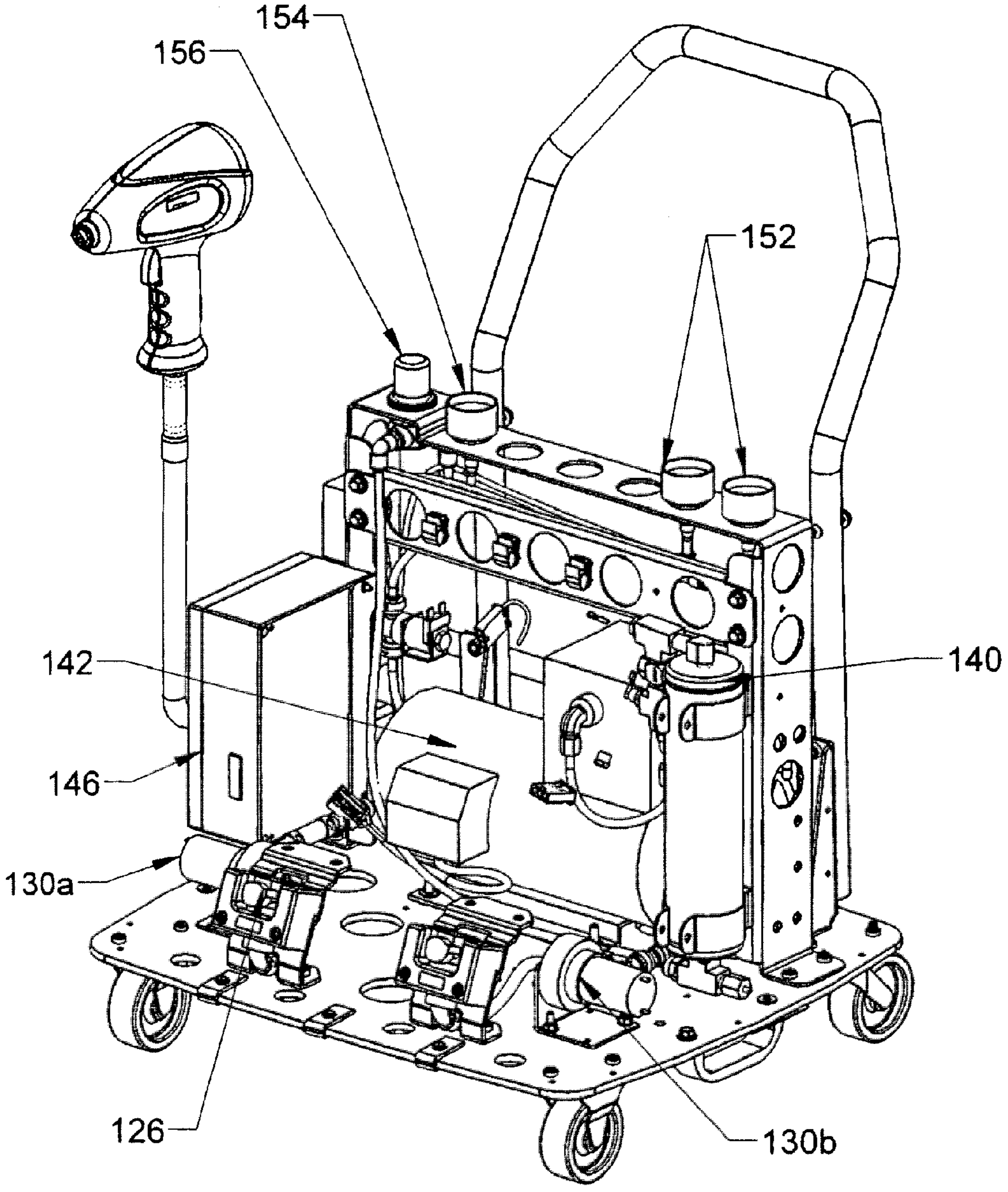
FIG. 6 is a simplified perspective view of the interior of the base unit 102 of one embodiment of the fluid spraying system 100.

FIG. 6 illustrates a simplified perspective view of the interior of the base unit 102 in one embodiment of the fluid spraying system 100. As shown in FIG. 6, the first and second pumps 130*a,b* are positioned adjacent to the first and second fluid containers 120*a,b*, (not shown) respectively. It will be appreciated, however, that one or both of the pumps 130*a,b* can be positioned anywhere in the base unit 102.

With reference back to FIG. 3, the fluid spraying system 100 can include first and second solution valves 132*a,b* provided in the sprayer assembly 104. The first valve 132*a* is provided along the fluid flow path $P_1$ upstream from the first pump 130*a*, while the second valve 132*b* is provided along the fluid flow path $P_2$ upstream from the second pump 130*b*. The valves 132*a,b* are configured to control fluid flow along their respective fluid flow paths $P_1$, $P_2$ For example, when the valves 132*a,b* are in an "open" position, fluid is permitted to flow therethrough. When the valves 132*a,b* are in a "closed" position, fluid is not permitted to flow therethrough. In one embodiment, the valves 132*a,b* are solenoid valves. It will be appreciated, however, that any other type of controllable valve may be utilized.

As discussed above, the hose 106 couples the base unit 102, which contains the pumps 130*a,b*, to the sprayer assembly 104, which contains the valves 132*a,b*. Specifically, the hose 106 contains first and second hoses or tubes 135*a,b* that fluidly couple the first and second pumps 130*a,b* to the first and second valves 132*a,b*, respectively, as shown in FIG. 3.

With continued reference to FIG. 3, the fluid spraying system 100 can further include a mixing chamber 136 and a nozzle 138 provided in or on the sprayer assembly 104. The mixing chamber 136 is provided along the fluid flow paths $P_1$, $P_2$ upstream from the first and second solenoid valves 134*a,b*, while the nozzle 138 is provided upstream from the mixing chamber 138. The mixing chamber 136 is configured to permit the first and second fluids $F_1$, $F_2$ flowing along the fluid flow paths $P_1$, $P_2$, respectively, to combine and/or mix therein. For example, if the first and second fluids $F_1$, $F_2$ employed in the system 100 are different fluids, the two fluids can combine and/or mix in the mixing chamber 136 before entering the nozzle 138. The nozzle 138 is configured to eject the fluid, which is combined in the mixing chamber 136, onto an application surface.

In one embodiment, the fluid spraying system 100 can include an air tank 140 and an air compressor 142 provided in the base unit 102, as illustrated in FIG. 3. The air compressor 142 is configured to compress the air stored in the air tank 140 to provide a pressurized source of air along an air flow path A, which extends from the air compressor 142 through the hose 106 to the sprayer assembly 104. This air can then be used to atomize the first and second fluids $F_1$, $F_2$ that is ejected from the nozzle 138.

With continued reference to FIG. 3, the fluid spraying system 100 can include an air valve 144 provided in the base unit 102. The valve 144 is configured to control air flow along the air flow path A. For example, when the valve 144 is in an "open" position, air is permitted to flow therethrough. When the valve 144 is in a "closed" position, air is not permitted to flow therethrough. In one embodiment, the valve 144 can be a solenoid valve, although any other type of controllable valve may suffice.

As discussed above, the hose 106 couples the base unit 102, which contains the air tank 140, the air compressor 142, and the air valve 144, to the sprayer assembly 104, which contains the nozzle 138. Specifically, the hose 106 contains a hose or tube 145 that fluidly couples the air compressor 142 to the nozzle 138.

As shown in FIG. 3, the air flow path A terminates at the mixing chamber 136 or at nozzle exit 138. In the mixing chamber 136 or at the nozzle exit 138, the pressurized air combines and/or mixes with at least one fluid when one or both of the valves 132*a,b* and the valve 144 are in the open position. The combination and/or mixture of pressurized air and fluid creates an atomized mist of fluid that is ejected from the nozzle 138.

In one embodiment, the fluid spraying system 100 can include a controller 146 provided in the base unit 102 as shown in FIG. 3. The controller 146 is configured to control the operation of the fluid spraying system 100. Specifically, the controller 146 is configured to operate the pumps 130*a,b*, the solution valves 132*a,b*, the air compressor 142, and the air valve 144. Suitable controllers can include a processor, a microprocessor, a control circuit, a PLC, or any other appropriate control device.

With continued reference to FIG. 3, the fluid spraying system 100 can include an activation device 148 provided on the sprayer assembly 104. The activation device 148 is configured to activate the sprayer assembly 104 to eject fluid from the nozzle 138. The activation device 148 is in signal communication with the controller 146 via electronic cables or wires provided in the hose 106. Alternatively, the activation device 148 can communicate with the controller 146 through radio signals, infrared signals, or other wireless communication means. The activation device 148 can be in the form of a trigger switch, a dial, a toggle switch, a lever, a knob, a button, or any other appropriate device.

In one embodiment, the fluid spraying system 100 can include an input device 150 provided on the sprayer assembly 104 as shown in FIG. 3. The input device 150 is configured to control the spray intensity of the fluid through the nozzle 138. The input device 150 is in signal communication with the controller 146 via electronic cables or wires provided in the hose 106. Alternatively, the input device 150 can communicate with the controller 146 through radio signals, infrared signals, or other wireless communication means. The input device 150 can take the form of one or more dials, toggle switches, levers, knobs, buttons, or any other appropriate control device.

Alternatively, the sprayer assembly 104 would not include an input device. Instead, the activation device 148 can be further configured to adjust spray intensity. For example, the activation device 148 can be a trigger switch configured such that the intensity of the spray is increased as the trigger is further depressed. In another embodiment, the sprayer assembly 104 can employ a dial (not shown) configured to activate the sprayer assembly 104 and control the intensity of the spray. In this embodiment, a user can rotate the dial to a first position to activate the fluid spraying system 100 at a low intensity level, then further rotate the dial to increase the spray intensity.

Figure 7A:
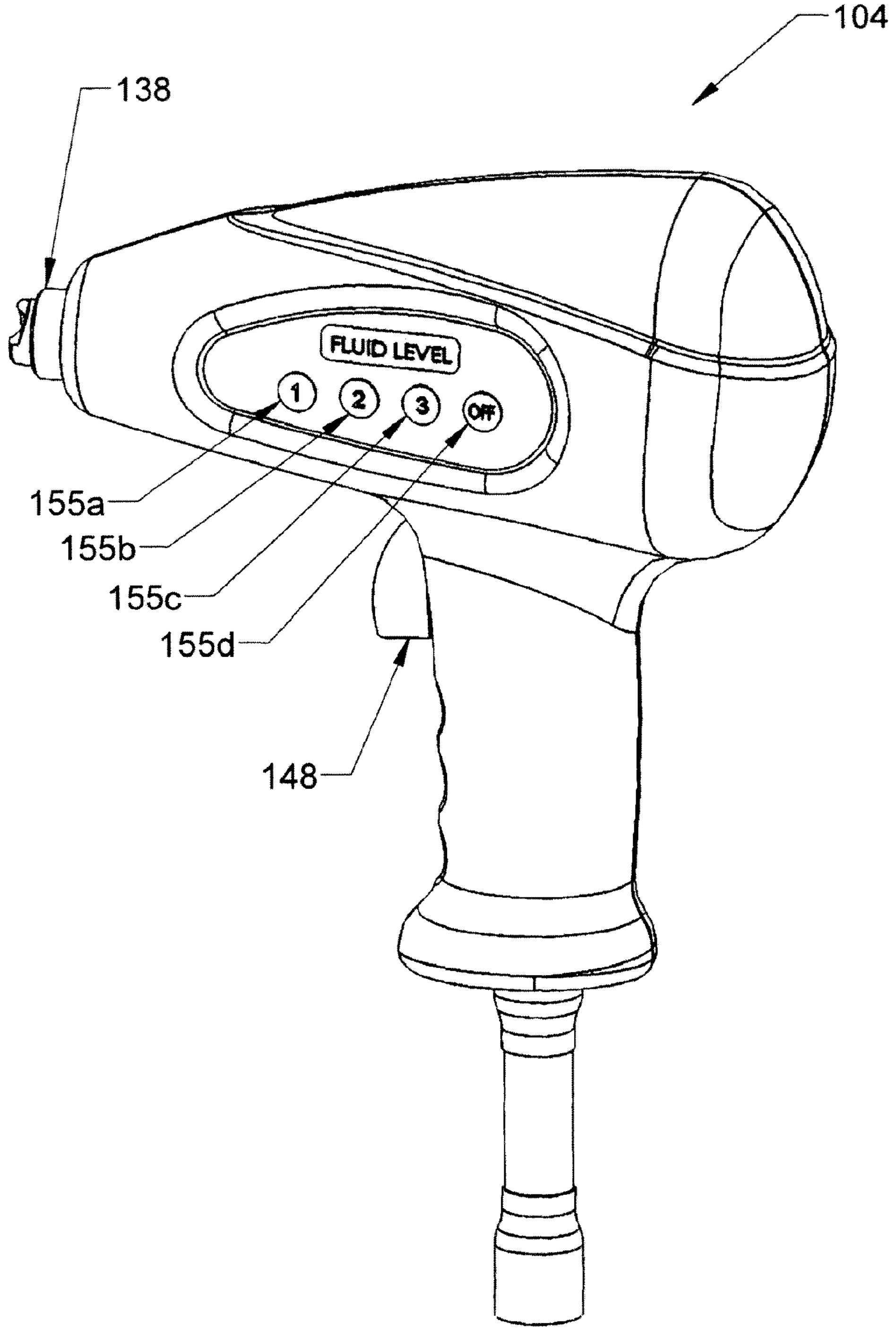
FIG. 7A is a perspective view of the sprayer assembly 104.

FIG. 7A illustrates a detailed perspective view of one embodiment of the sprayer assembly 104. In one embodiment, the activation device 148 can take the form of a trigger switch and the input device 150 can take the form of four pushbuttons 155*a-d* disposed along the side of the sprayer assembly 104 as shown in FIG. 7A. In the exemplary embodiment, each pushbutton 155*a-d* can be configured to transmit a selection of a pre-set intensity level to the controller 146. For example, a first pushbutton 155*a* can be activated to select a low intensity level, a second pushbutton 155*b* can be activated to select a medium intensity level, a third pushbutton 155*c* can be activated to select a high intensity level, and a fourth pushbutton 155*d* can be activated to select an intensity level of zero. If the user selects an intensity level of zero, the controller 146 will not operate the pumps 130*a,b*, but will operate the air compressor 142 so that only air is sprayed through the nozzle 138. Additionally, the pushbuttons can be programmable by the user.

With reference back to FIG. 3, the fluid spraying system 100 can include an input/output device 118 such as an LCD touchpad display provided on the base unit 102 to allow a user to select a ratio of solutions to create a desired solution mixture. In one embodiment, the LCD touchpad display can also be configured to allow a user to select a spray intensity level or can be used to program the push buttons 155*a-d* provided on the sprayer assembly 104 for spraying intensity level. The LCD touchpad display is in signal communication with the controller 146. It will be appreciated that in addition to, or instead of, the LCD display, an input device can be provided on the sprayer assembly 104 to allow a user to select a desired solution mixture.

Furthermore, it will be appreciated that the LCD touchpad display can perform additional functions. For example, the LCD touchpad display can be used to track an operator name, spray time, and solution usage and store this data in memory. The LCD touchpad display can also monitor all output functions including, but not limited to, air pressure, solution pressure, pump currents, and solenoid valve operation.

It will also be appreciated that the fluid spraying system 100 can include additional input or output devices disposed on the base unit 102. For example, as shown in FIG. 6, fluid pressure gauges 152 are provided at the top of the base unit 102 to indicate the fluid pressure of each fluid in the fluid containers 120*a,b*. Also, an air pressure gauge 154 can be provided at the top of the base unit 102 to indicate the air pressure. Additionally, an air pressure regulator 156 can be provided at the top of the base unit 102 to allow the user to regulate the air pressure.

In an alternative embodiment not illustrated in the drawings, an atomized spray of fluid can be created without the use of compressed or pressurized air. In this embodiment, the fluid spraying system 100 would not include the air tank 140, the air compressor 142, or the air valve 144. Instead, the system 100 would include a high pressure pump (not shown) for each fluid container 120*a,b* and the sprayer assembly 104 would employ a hydraulic atomizing nozzle (not shown) to create an atomized mist of fluid. It will be appreciated that this embodiment be used with a single fluid container or more than two fluid containers.

In an alternative embodiment not illustrated in the drawings, an atomized spray of fluid can be created without the use of compressed air. In this embodiment, the fluid spraying system 100 would not include the air tank 140 or the air compressor 142. Instead, the system 100 may include an HVLP (high velocity/low pressure) fan (not shown) in connection with the air valve 144 (optional in this embodiment). The air flow from this fan would be in fluid communication with the nozzle 138. This air flow may be used to atomize the fluid at the nozzle 138.

The fluid spraying system 100 can include additional components without departing from the scope of the present application. For example, the system 100 can include fluid detection sensors 158 disposed near the bottom of each fluid container 120*a,b* as shown in FIG. 6. The fluid detection sensors 158 are configured to sense the solution level in each fluid container 120*a,b*. When the solution level falls below a predetermined threshold, the fluid detection sensors 158 can be configured to transmit a signal to the controller 146. Upon receipt of the signal, the controller 146 can deactivate the fluid spraying system 100 to prevent air from being pulled into one or both of the fluid flow paths $P_1$, $P_2$. Exemplary fluid detection sensors that can be employed include capacitive solution detection switches, optical sensors, or piezoelectric sensors.

Also, the fluid spraying system 100 can include a heating element (not shown), such as a heating coil or other heating device, that can be placed around or adjacent to the first and/or second fluid tubes 135*a,b* to heat the fluid flow paths $P_1$, $P_2$, thereby creating a warm, atomized mist of fluid that can be ejected from the nozzle 138. Additionally, a heating element can be placed around or adjacent to the air tube 145 to heat the air flow path A. Alternatively, heating elements can be placed around or adjacent to one or both of the fluid containers 120*a,b*.

In yet another embodiment, the base unit 102 can include a power switch (not shown) to activate the controller 146. The power switch can be of the form of a toggle switch, a dial, a knob, a pushbutton, or any other appropriate device. In one embodiment, the power switch can be further configured to activate the air compressor 142. Therefore, in this embodiment, the activation of the trigger switch 146 would not cause the activation of the air compressor 142, nor would the release of the trigger switch cause the deactivation of the air compressor 142.

Figure 7B:
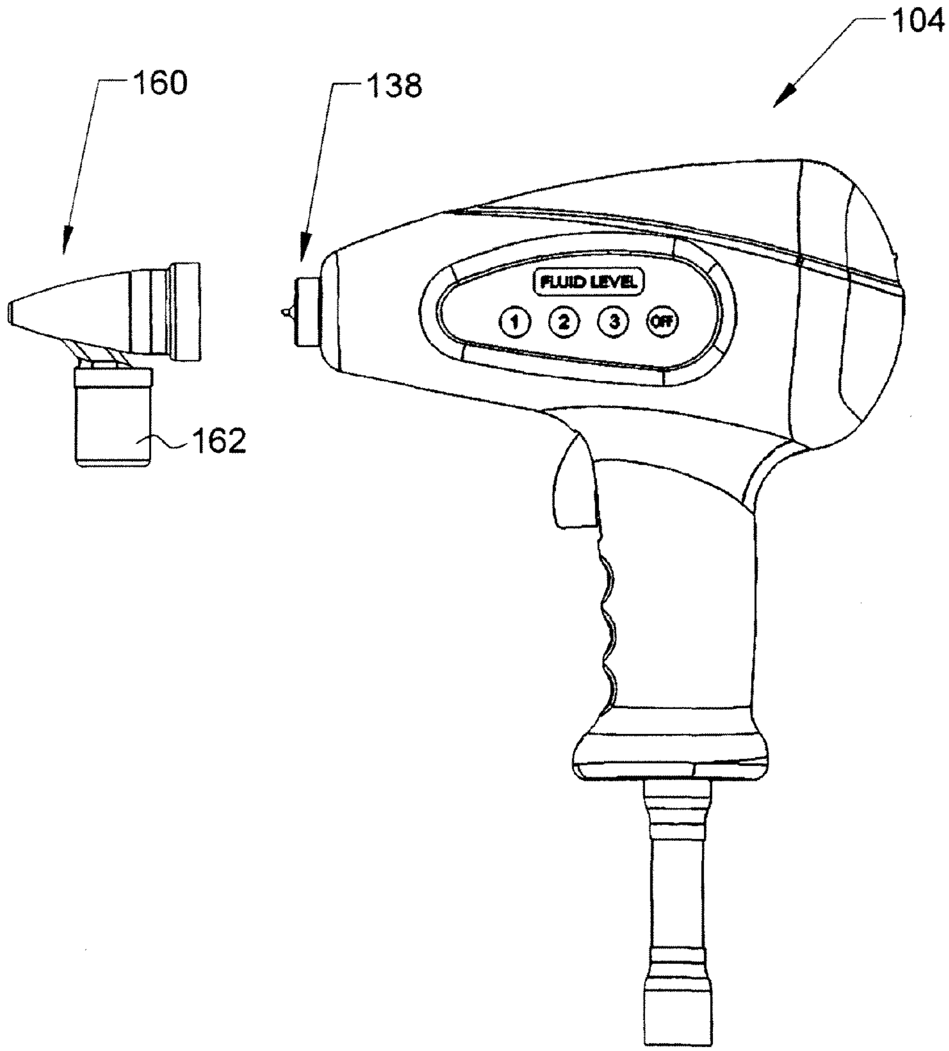
FIG. 7B is a perspective view of the sprayer assembly 104 and an optional attachment accessory 160.

In yet another embodiment, the fluid spraying system 100 can include an attachment accessory 160 as shown in FIG. 7B. The attachment accessory 160 is configured to be removably attached to the nozzle 138 of the sprayer assembly 104 via a threaded connection. The attachment accessory 160 includes an auxiliary fluid reservoir 162 that is configured to contain an auxiliary fluid. The attachment accessory 160 is configured to channel air from the sprayer assembly through the tip of the nozzle 138 and adjustably siphon the auxiliary fluid from the auxiliary fluid reservoir 162 so that the auxiliary fluid can be sprayed onto an application surface. Exemplary auxiliary fluids include temporary tattoo dye, paint, other tanning solutions, or any other media that can and is desired to be sprayed.

Figure 8A:
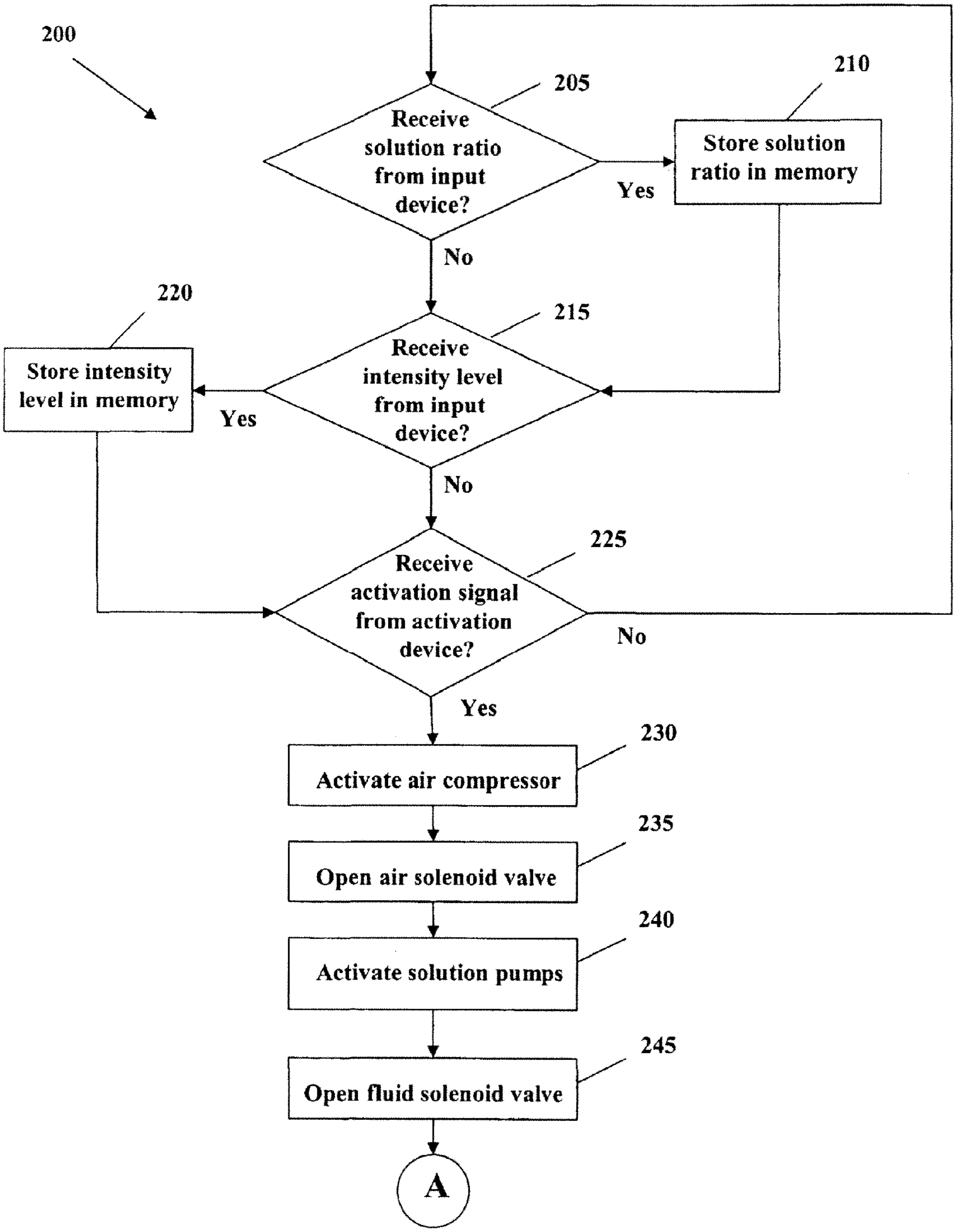
FIGS. 8A and 8B are flow charts illustrating one method 200 for operating the fluid spraying system 100 that can be employed by a controller.
Figure 8B:
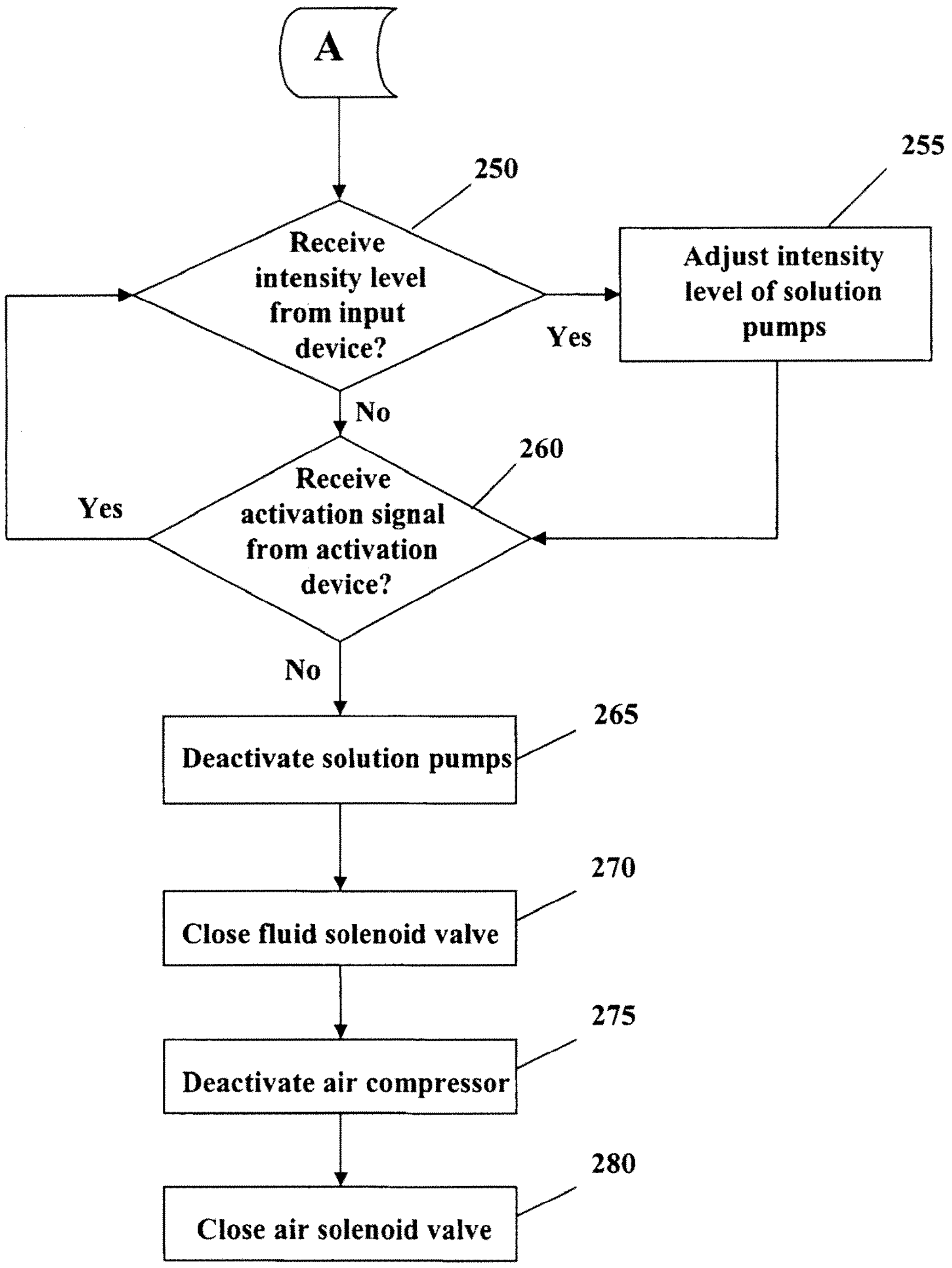

FIGS. 8A and 8B illustrate a flow chart diagram of an exemplary method 200 for operating the fluid spraying system 100 employed by the controller 146. The controller initially waits for a user to input a desired fluid ratio (step 205). If the user selects a fluid ratio via an input device, the input device transmits a signal to the controller, and the controller stores the selected fluid ratio in a memory (step 210). The controller also waits for a user to input an intensity level (step 215). If the user selects an intensity level via an input device, the input device transmits a signal to the controller, and the controller stores the selected intensity level in a memory (step 220). It will be appreciated that the fluid spraying system employ a single input device, such as an LCD touchpad, to receive input related to the fluid ratio and spray intensity. Alternatively, the fluid spraying system can employ separate input devices, such as an LCD touchpad disposed on the base to receive input related to the fluid ratio and pushbuttons disposed on the sprayer assembly to receive input related to the spray intensity.

The controller also waits for the user to activate the fluid spraying system (step 225). When the user activates an activation device, the activation device transmits a signal to the controller. Upon receipt of the signal from the activation device, the controller activates the air compressor (step 230) and opens the air solenoid valve (step 235) to allow air to spray from the air tank through the nozzle of the sprayer assembly via a hose. The controller then activates the pumps (step 240). If the user has selected a fluid ratio and/or an intensity level, the controller operates the pumps according to the levels stored in the memory. If the user has not made a selection prior to activation, the controller can be programmed to operate the pumps at default levels or at the levels last stored during a prior operation of the fluid spraying system. The controller then opens appropriate fluid solenoid valves (step 245). However, it will be appreciated that steps 230-245 can be performed in any order.

If the user has selected a fluid ratio that includes both fluids, the two fluids and the compressed air mix in a mixing chamber in the sprayer assembly to create an atomized mist that sprays through the nozzle of the sprayer assembly. If the user has selected a single fluid, the single fluid and the compressed air mix in the mixing chamber in the sprayer assembly to create an atomized mist that sprays through the nozzle of the sprayer assembly.

During operation of the sprayer assembly, the user can select a different intensity level (step 250). If the user inputs a new intensity level, the input device will transmit a signal to the controller, and the controller will adjust the intensity level of the pumps (step 255). The fluid spraying system will continue to spray fluid for as long as the user activates the activation device (step 260). When the trigger switch is released, or the activation device is otherwise deactivated, the controller deactivates the pumps (step 265) and closes the fluid solenoid valves (step 270). The controller then deactivates the air compressor (step 275) and closes the air solenoid valve (step 280) to stop the spraying. It will be appreciated that steps 265-280 can be performed in any order.

Figure 9:
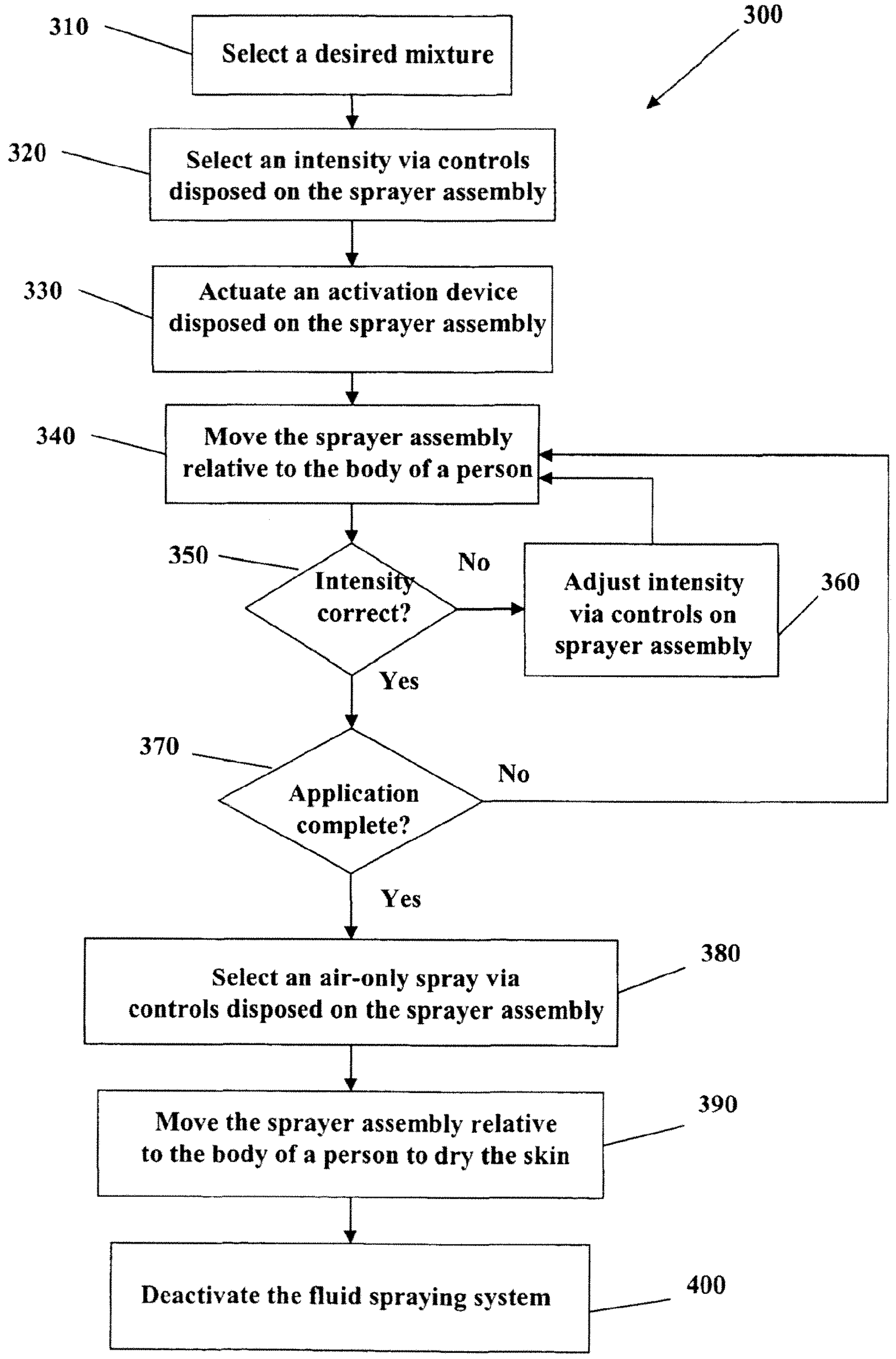
FIG. 9 is a flow chart illustrating one method 300 for applying a solution to a human body that can be employed by an operator of the fluid spraying system 100.

FIG. 9 illustrates a flow chart diagram of one method 300 for applying a solution (such as a sunless tanning solution) to a human body that can be employed by an operator of the fluid spraying system 100. In the illustrated method of operation, the operator can transport the fluid spraying system to a recipient's home or any other location. The operator or recipient selects a solution ratio according to the recipient's preference by using an LCD touchpad display or other appropriate input device (step 310). The operator or recipient then selects a spray intensity level by pressing an appropriate pushbutton on the sprayer assembly or using another appropriate input device (step 320). The operator then actuates an activation device, such as a trigger switch, to spray an atomized mist of tanning solution from the nozzle of the sprayer assembly (step 330). Next, the operator moves the sprayer assembly relative to the recipient's body to apply the solution as desired or as instructed by the recipient (step 340). During the spraying of the solution, the operator and/or the recipient determines if the intensity should be adjusted (step 350). For example, the operator or recipient can determine that a certain area of the body can require a darker or lighter shading than other areas to create contoured shading resulting in a natural looking tan. The operator can adjust the solution flow intensity accordingly during the operation (step 360). When the operator and/or recipient determines that the coating is complete (step 370), the operator can optionally select a spray intensity of zero to create an air-only spray (step 380). The operator can then move the sprayer assembly relative to the recipient's body to dry the skin (step 390). When the skin has been satisfactorily dried, the operator can then deactivate the fluid spraying system (step 400).

It will also be appreciated that the base unit 102 of the fluid spraying system 100 need not be in the form of a mobile cart. For example, in one embodiment, the base unit 102 could be a portable system that does not include wheels, but rather includes a carrying handle to allow a user to transport the fluid spraying system 100. Alternatively, the base unit 102 can be stationary or in other words, not portable. For example, the base unit 102 can be a booth having a door. The booth can also be an open design. The booth could house at least one fluid reservoir and would include a sprayer assembly (similar to the one described above) in fluid communication with the fluid reservoir via a hose. In this embodiment, a user could enter the booth and an operator could apply sunless tanning solution to the user's body using the sprayer assembly. In another embodiment, the booth can include stationary nozzles to automatically apply sunless tanning solution to the user's body, then the user can supplement or "touch up" the application by using the sprayer assembly. In either embodiment, the booth can include an optional fan or fans for removing residual spray.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus, and illustrative examples shown and described.

Accordingly, departures can be made from such details without departing from the spirit or scope of the applicant's general inventive concept. The system is not designed solely for sunless tanning products or for the purpose of spraying a human body. It can accommodate almost any type of product being sprayed.

What is claimed is:

1. A container for use in a system for spray coating a human subject, the container comprising:

a container body configured to hold a skin coating composition;

a first end portion having a male disconnect coupling valve, where the male quick disconnect coupling valve is configured to open when coupled to a female fitting disposed in a spraying apparatus, where the male quick disconnect coupling valve is further configured to prevent flow of the skin composition from the container in an inverted position while the male quick disconnect coupling valve is not coupled to the female fitting; and a second end portion opposite the first end portion, where the container is configured for inverted connection to the spraying apparatus such that when the male quick disconnect coupling valve is connected to the female fitting, the male quick disconnect coupling valve permits flow of the skin composition from the container after pressure is equalized in the container, the male quick disconnect coupling valve is at a location below the second end portion, and where opening of a vent on the second end portion allow airflow into the container through the vent as the skin coating composition flows out of the container through the male quick disconnect coupling valve.

2. The container of claim 1, where the container is configured as a reservoir for the skin coating composition such that when the container is connected to the spraying apparatus the skin coating composition may flow out of the container through the male quick disconnect coupling valve and out of at least one nozzle in the spraying apparatus.

3. The container of claim 1, further comprising a solution including at least one ingredient selected from the group consisting of dihydroxyacetone, crotonaldehyde, pyruvaldehyde, glycolaldehyde, glutaraldehyde, otho-phthaldehyde, sorbose, fructose, erythrulose, methylvinylketone, food coloring and a bronzer.

4. The container of claim 1, where the second end portion further includes a container base, where the vent is substantially recessed into the container base the inside of the container such that the container may rest on a substantially flat surface with the container base supporting the container while the container base is substantially parallel to the surface.

5. The container of claim 1, where the container is configured for use in combination with a second container such that the spraying apparatus sprays onto the human subject a mix of the skin coating composition held by the container and a second skin coating composition held by the second container.

6. The container of claim 1, where the container is configured for use in combination with a second container such that the spraying apparatus first sprays onto the human subject the skin coating composition held by the container and second a second skin coating composition held by the second container.

7. The container of claim 1, where the vent includes a check valve configured to prevent any solution from leaking out through the vent when the fluid container is disconnected from the spraying apparatus.

* * * * *